United States Patent [19]
Beaver et al.

[11] 3,967,194
[45] June 29, 1976

[54] METHOD FOR FLAW LOCATION IN A MAGNETIZABLE PIPELINE BY USE OF MAGNETIC MARKERS POSITIONED OUTSIDE OF SAID PIPELINE

[75] Inventors: Ruby C. Beaver, Houston, Tex.; Theodor Clasen, Wienhausen; Wolfgang Henning, Celle, both of Germany; Emil S. Johnson, Houston, Tex.

[73] Assignee: Vetco Offshore Industries, Ventura, Calif.

[22] Filed: Jan. 8, 1975

[21] Appl. No.: 539,398

Related U.S. Application Data

[60] Division of Ser. No. 451,505, March 15, 1974, Pat. No. 3,899,734, which is a continuation-in-part of Ser. No. 360,161, May 14, 1973, abandoned.

[52] U.S. Cl. .............................. 324/37; 346/33 P; 346/33 F
[51] Int. Cl.² ...................................... G01R 33/12
[58] Field of Search ............... 324/34 R, 37, 40, 67; 346/33 P, 33 F; 73/40.5 R

[56] References Cited
UNITED STATES PATENTS

| | | | |
|---|---|---|---|
| 3,060,315 | 10/1962 | Scherbatskoy | 73/40.5 R |
| 3,116,452 | 12/1963 | Schmidt | 324/37 |
| 3,162,505 | 12/1964 | Hall | 346/33 P |
| 3,413,653 | 11/1968 | Wood | 346/33 P |

*Primary Examiner*—Robert J. Corcoran
*Attorney, Agent, or Firm*—Vinson, Elkins, Searls, Connally & Smith

[57] ABSTRACT

A magnetic flux leakage method and apparatus for inspecting magnetizable test objects such as pipelines are disclosed. Magnetic diodes are connected to give temperature-independent readings of flux leakage and are spaced apart according to the size of the flaws sought to be detected. Groups of diodes are overlapped to provide complete coverage of the area sought to be inspected. Certain of the largest signals received at any one time from the groups of diodes are transmitted to recording means to reduce the number of signals recorded. Diode signals are subtracted from each other to determine relative differences in detected fluxes. For inspecting pipelines, the diodes and magnets are mounted on the apparatus by mounting assemblies which pivot about three axes and the diodes and magnets are urged yieldingly toward the pipeline wall by members formed of open cell foam polyurethane. To aid in locating the flaws along the pipeline, signals from magnetic markers placed along the pipeline are detected and recorded with signals from flaws. This abstract is not to be construed in any way to define or limit the invention set forth below.

8 Claims, 21 Drawing Figures

METHOD FOR FLAW LOCATION IN A MAGNETIZABLE PIPELINE BY USE OF MAGNETIC MARKERS POSITIONED OUTSIDE OF SAID PIPELINE

PRIOR APPLICATION

This is a divisional application of our application Ser. No. 451,505, filed Mar. 15, 1974, now U.S. Pat. No. 3,899,734, which is a continuation-in-part of application Ser. No. 360,161, filed May 14, 1973 and now abandoned.

BACKGROUND OF THE INVENTION

1. Field

This invention relates to detecting flaws in magnetizable test objects by measuring the magnetic flux leakage caused by such flaws. The invention particularly relates to inspection apparatus which may be referred to as inspection pigs and which are adapted to be run through and to inspect buried pipelines which transmit petroleum products and other fluids. These inspection pigs are designed to provide information about the pipeline's deterioration (such as pits and cracks caused by corrosion, stress or other causes) without the relatively great cost of unearthing the pipeline. This information is particularly important because buried pipeline is expensive and because a pipeline explosion can destroy adjacent property and take human lives.

2. Prior Art

A used throughout this description and in the claims, the terms "magnetize" and "magnetizing" and related terms refer to the concept of introducing a magnetic field or magnetic flux into a region or object. The inspection of a magnetizable test object by magnetizing the object and measuring the magnetic flux leakage adjacent the object and caused by flaws in the object is relatively old in the art. For example, U.S. Pat. No. 1,867,685 (1932) to Sperry discloses such a device for railway rails. Further, inspection pigs for inspecting various conditions in pipelines have been known for over ten years. See, for example, U.S. Pat. No. 2,782,370 (1957) to Ver Nooy and U.S. Pat. No. 3,064,127 (1962) to Green et al.

Inspection apparatus generally referred to as inspection pigs typically are propelled through a pipeline by the pressure of the fluids therein and thus may go through a pipeline without substantially disrupting its operation. These pigs frequently comprise one or more supports, annular cups attached to the supports and engaging the inner wall of the pipeline, magnets mounted on a support for magnetizing the pipeline, detectors mounted adjacent the magnets for measuring the flux leakage, and recorders, such as strip charts and pens, mounted on a support for recording the flux leakage measurements.

In the known prior art, several basic sensing means or detectors have been used to sense flux leakage. Moving a current-conducting wire through a magnetic field will induce in the wire electric current proportional to the speed of movement and the strength of the magnetic field. This type of detector has broad application but has the obvious disadvantages that the wire must be moving with respect to the magnetic field to produce a reading and that the amplitude of the reading will be proportional to the velocity of the wire. Detectors such as Hall elements and magnetometers do not depend on movement with respect to the magnetic field, but these devices are relatively complex and expensive, require relatively complex and expensive complimentary electronic circuitry and must be driven by a power source which adds weight and expense to the inspection device.

Magnetic diodes are relatively new semi-conductor devices which change their internal electric resistance as a function of an external magnetic field. They measure magnetic flux independently of their velocity with respect to the flux and are from 10 to 100 times more sensitive than Hall elements. Magnetic diodes are relatively simple and inexpensive and require relatively small amounts of power; however, they are quite small, typically having a length of no more than ¼ inch. Magnetic diodes may be connected in pairs to form twin diodes which function independently of temperature. Magnetic diodes are known to have a variety of applications suitable to their small size, such as generating pulses as disclosed in U.S. Pat. No. 3,689,836 (1972) to Snyder, providing a commutating device for a brushless direct current motor as disclosed in U.S. Pat. No. 3,688,172 (1972) to Sieber et al and detecting flux leakage from relatively small areas of movable test objects which are translated and rotated with respect to the diodes, as disclosed in U.S. Pat. No. 3,670,239 (1972) to Shiraiwa et al. However, because of their small size, magnetic diodes have no obvious application with test objects such as pipelines that are relatively immovable and relatively large as compared to the usual one-quarter inch size of said diodes.

In the prior art, problems have been encountered in maintaining the magnets and detectors in sufficiently close proximity to the test object to magnetize the test object and to detect magnetic flux leakage therefrom caused by defects therein. These problems are particularly acute with pipelines because the magnets and detectors should be maintained close to the pipeline wall, preferably at a constant distance therefrom, but should also be capable of moving radially inwardly and outwardly responsive to variations in the internal diameter of the pipeline without damaging the pipeline to accommodate decreases in the diameter of the pipeline caused by dents, welds and other obstructions. In the prior art, various spring mechanisms have been used to urge the magnets and detectors toward the pipeline, but these mechanisms have been unduly heavy and bulky, are subject to failure, require maintenance and are relatively expensive.

In the prior art, problems have been encountered in determining the location of pipeline flaws detected by a moving flux leakage inspection apparatus or pig, because the pig seldom travels through the pipeline at an even or known speed due primarily to changes in the terrain and pressure within the pipeline. Odometers attached to the pig in engagement with the interior wall of the pipeline can supply valuable information, but have been inaccurate because of slippage. U.S. Pat. No. 3,064,127 (1962) to Green et al discloses the use of radioactive markers placed at selected locations along a pipeline and U.S. Pat. No. 3,116,457 (1963) to Schmidt discloses the use of coil markers placed along a pipeline to influence eddy currents, but such markers clearly are not useful for inspection pigs depending on flux leakage detection. Magnetic markers placed at selected locations along the exterior of the pipeline to influence flux therein have many advantages, but in the prior art their signals were easily confused with signals caused by stopples, nipples and other hardware attached to the line and thus separate equipment has been required for detecting marker signals, thereby adding to the weight and cost of the pig.

SUMMARY

Applicants solve the problems associated with the flux detectors by providing flux sensing means or detectors which comprise a plurality of spaced apart twin magnetic diodes. These twin magnetic diodes preferably comprise at least two separate groups. The groups are spaced apart in overlapping relationship so that, while a substantial surface area is inspected by one passage of the diodes near the test object, even the smallest flaw sought to be detected will be detected by at least two twin diodes in one of the groups, and thus will give rise to a significant signal. Thus, the detectors function independently of their velocity with respect to the test object, have great sensitivity, are relatively simple and inexpensive and require relatively small amounts of power.

Applicants solve the problem of yieldingly maintaining the pig magnets and detectors in sufficiently close proximity to the interior wall of the pipeline to magnetize and inspect the pipeline by providing for the magnets and detectors mounting assemblies which pivot about three axes and by providing two annular members of open cell foam polyurethane, foam rubber or a similar elastomeric material. These members are mounted on the inspection apparatus yieldingly to urge the magnets and detectors toward the interior wall of the pipeline. The open cell foam polyurethane or similar material is light, inexpensive, easy to maintain and does not require the space of an expanding and contracting spring mechanism.

Applicants solve the problem of detecting, without additional sensing means or detectors, magnetic markers placed at selected locations along and exterior to the pipeline by placing the markers with selected orientations with respect to the pipeline so that the markers will have a predictable influence on the flow of magnetic flux measured by the magnetic diodes in the interior of the pipeline. In the preferred embodiment, the markers are magnets oriented in opposed relationship to the pig magnets so that as the pig magnets pass by the markers, the flux measured by the magnetic diodes first increases, then decreases and then increases again, as the markers alter the flow of flux between the poles of the pig magnets. The magnetic diode signals from the reduction in flux flow caused by the markers are processed separately from the diode signals from flux variations caused by flaws and then are recorded separately from but adjacent to the flaw signals. Thus, no additional detectors are needed to detect the markers.

An object of this invention is to provide a magnetic flux leakage inspection apparatus having sensing means or detectors which are sensitive, simple, inexpensive, which have low power requirements, which can measure magnetic flux leakage independently of the speed of the apparatus with respect to the flux leakage, which can inspect relatively large surface areas at one time and which can inspect immovable test objects.

Another object of the invention is to provide an electromagnetic pipeline inspection device having magnets and detectors wherein the magnets and detectors are mounted on the device by mounting assemblies which pivot about three axes and wherein the magnets and detectors are yieldingly urged against the interior wall of the pipeline by a light, compact, easy-to-maintain and inexpensive member which keeps them in close and constant proximity to the interior wall of the pipeline but permits the passage of the device through narrow portions of the pipeline.

Another object of the invention is to provide a method and apparatus for detecting magnetic markers along the pipeline to provide information as to the location of the detected flaws without the necessity of providing additional sensing means to detect the markers.

Other objects will be apparent from the drawings, the specifications and the claims.

BRIEF DESCRIPTION OF THE DRAWINGS

In the drawings wherein like reference numerals indicate like parts and wherein the illustrative embodiments of this invention are shown:

FIG. 8 is a schematic illustration of one of the magnetic diodes;

DESCRIPTION OF THE PREFERRED EMBODIMENTS

Figure 1:
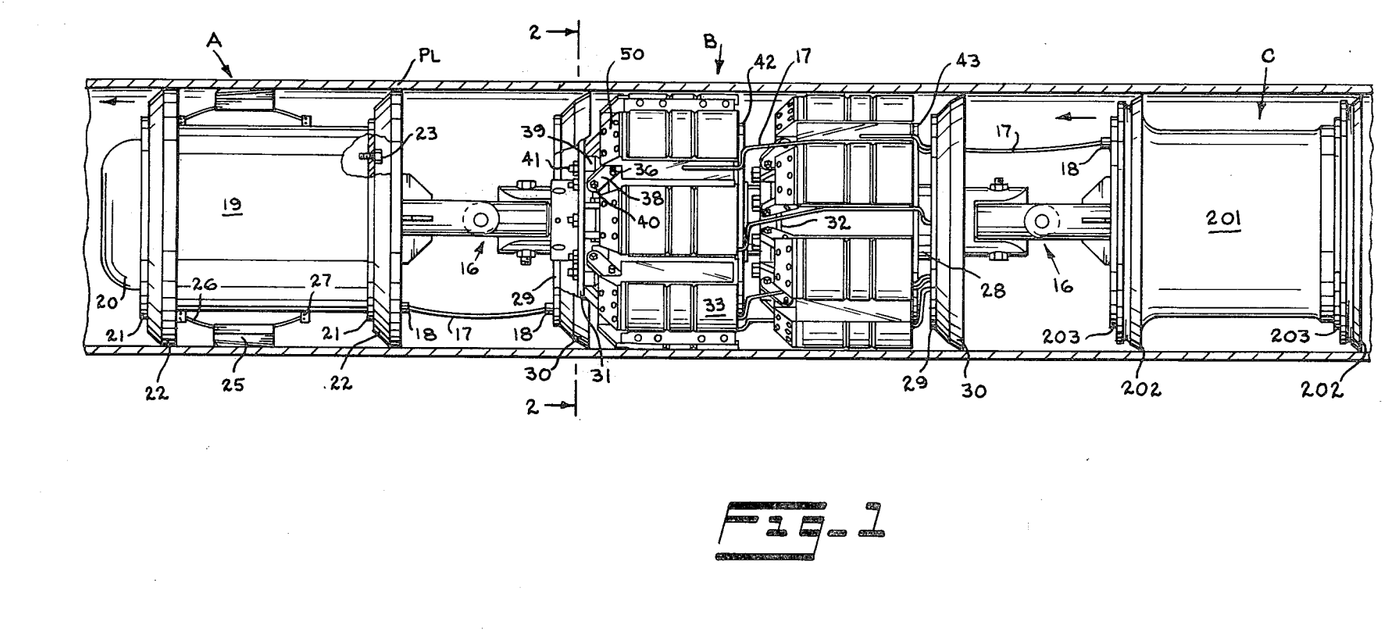
FIG. 1 is a view partly in elevation and partly in section of a pipeline inspection apparatus embodying the invention and in place within the pipeline.

FIG. 1 shows an inspection apparatus or pig embodying the invention and adapted to be run through a pipeline PL in the direction indicated by the arrows. The apparatus includes three sections: a battery capsule A at the downstream end, a magnet module B in the central portion of the apparatus and a recorder capsule C at the upstream end. These three sections are joined together in tandem by a pair of universal joints 16 which enable the device to negotiate relatively sharp bends in the pipeline.

The battery capsule A carries sufficient batteries to provide the necessary power for the other components of the apparatus or pig. The magnet module B contains magnets for magnetizing the pipeline and sensing means or detectors for detecting magnetic flux in the pipeline. The recorder capsule C houses equipment for processing and recording signals from the detectors. Conductor means 17 which are shown only in part are provided for conducting electric current and signals through plugs 18 and between the battery capsule A, the magnet module B and the recorder capsule C.

The battery capsule A includes a support or mandrel 19, a bumper nose 20 mounted on the downstream or forward end of the mandrel 19, and spaced-apart plates 21 attached by suitable means, such as welding, to the ends of mandrel 19. Annular cups 22 are mounted on the plates 21 by suitable securing means, such as bolts 23. The cups 22 obstruct the annulus between the mandrel 19 and the interior wall of the pipeline PL; these cups support the battery capsule A in the center of the pipeline PL and, together with other elements of the pig, provide resistance to the flow of fluid through the pipeline and thus constitute propelling means for moving the pig through the pipeline when said fluid impinges on the pig.

A plurality of vanes 25 are mounted on the mandrel 19 by spring legs 26 which yieldingly extend the vanes toward and into contact with the interior wall of the pipeline PL. As shown, each spring leg 26 is connected at each end to lugs 27 on the mandrel 19. The vanes 25 and the spring legs 26 constitute rotator assemblies which gradually rotate the pig about its longitudinal axis as it travels through the pipeline, thus promoting even wear of the pig.

Figure 2:
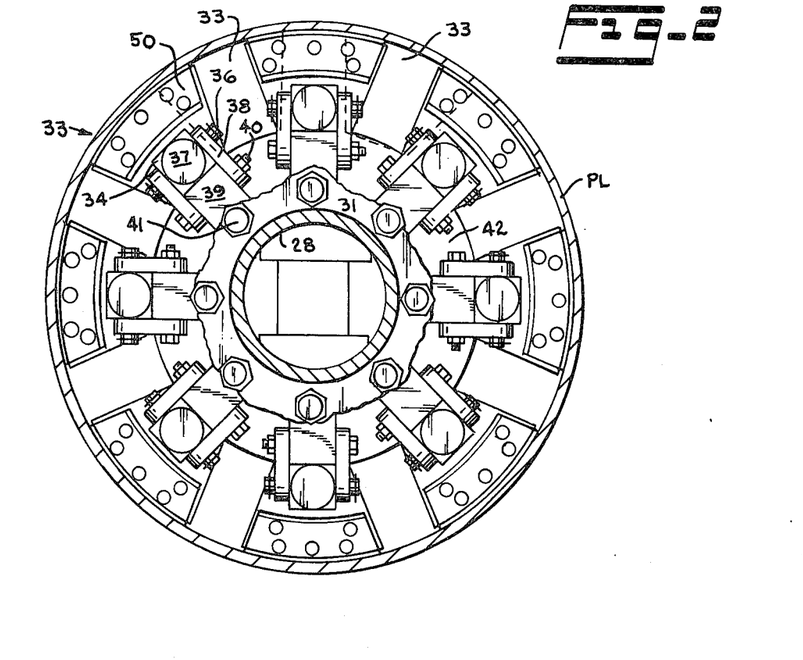
FIG. 2 is a cross-sectional view taken along line 2—2 in FIG. 1.

The magnet module B includes a longitudinally extending central support or mandrel 28. On each end of said mandrel are mounted plates 29 and cups 30 similar in size and function to the plates 21 and cups 22 of the battery capsule A. Annular plates 31 and 32 are mounted by suitable means, such as welding, at the downstream end and midsection respectively of mandrel 28 and form annular bases for pivotally mounting on the mandrel 28 16 magnet assemblies 33 in two sets of eight magnet assemblies each. Each set is located in an annular path about the mandrel and can be said to form a ring of magnet assemblies. Each of these two sets extends along the entire inner wall of the pipeline, as is seen best in FIG. 2. As shown in FIGS. 1 and 2, the two sets of magnet assemblies 33 are circumferentially offset from each other by about 22½° so that the 16 magnet assemblies will cover the entire wall of the pipeline as the apparatus or pig passes through the pipeline. Applicants have found that the turning radius of the pig may be reduced even further when appropriate by providing a mandrel 28 which comprises two sections joined by a suitable universal joint not shown in the drawings, but mounted between the two sets of magnet assemblies, just downstream of annular plate 32.

The recorder capsule C similarly includes a central support or mandrel 201, cups 202 and plates 203, similar in size and function to those of capsule A and module B.

If desired, an odometer may be mounted on the pig for the purpose of aiding in the determination of the location of pipeline flaws detected by the pig. As discussed above, the use of such odometers is old and is not completely satisfactory because of slippage. However, an odometer may be a material aid in locating flaws, particularly when used in combination with other techniques such as magnetic markers. Applicants have discovered that the use of an odometer of the general character shown in U.S. Pat. No. 3,732,625 to Ver Nooy can be appropriate. This odometer, not shown in the drawings, comprises an arm having an inner end and an outer end. The inner end is mounted pivotally to the upstream end of mandrel 201 behind the upstream cup 202. The outer end carries a rotatable wheel whose rim engages the interior wall of the pipeline PL upstream of mandrel 201. Springs attached to mandrel 201 and to the arm continually urge the wheel against the pipeline PL. A small magnet is fixed to the wheel and magnetic flux sensing means such as magnetic diodes are mounted on the arm so that the magnet will pass by the sensing means once every time the wheel completes a revolution. Thus, the sensing means will generate a signal for every revolution. These signals, which of course are indications of the distance traveled by the pig, are recorded by the recording apparatus described below and may be displayed on a strip chart with flaw signals.

Figure 3:
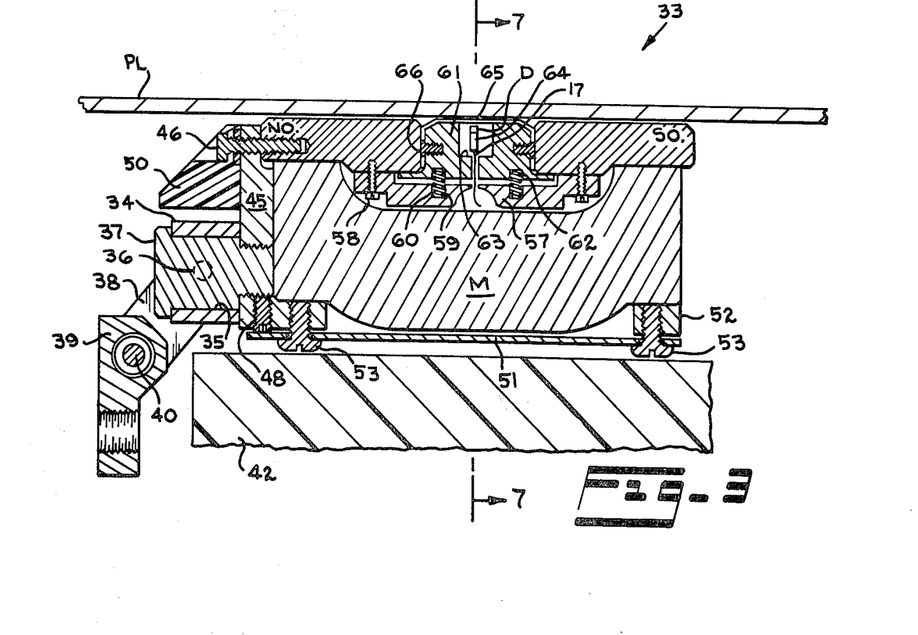
FIG. 3 is an enlarged, longitudinal, cross-sectional view taken through the center of one of the magnet assemblies and its mounting assembly.
Figure 4:
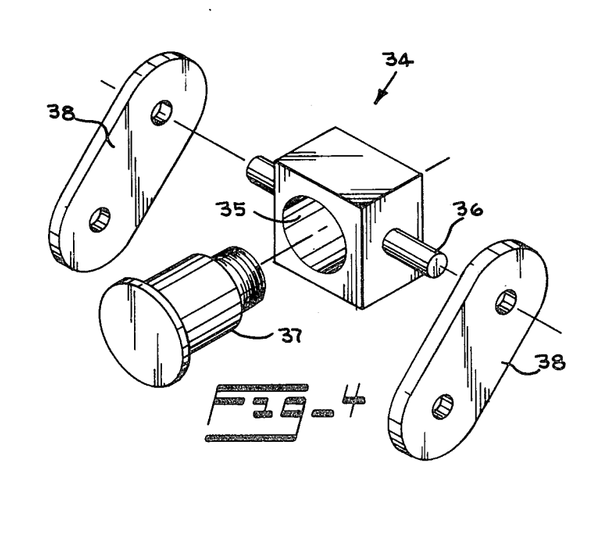
FIG. 4 is an enlarged, exploded, perspective view showing part of a mounting assembly for a magnet assembly.
Figures 5, 6:
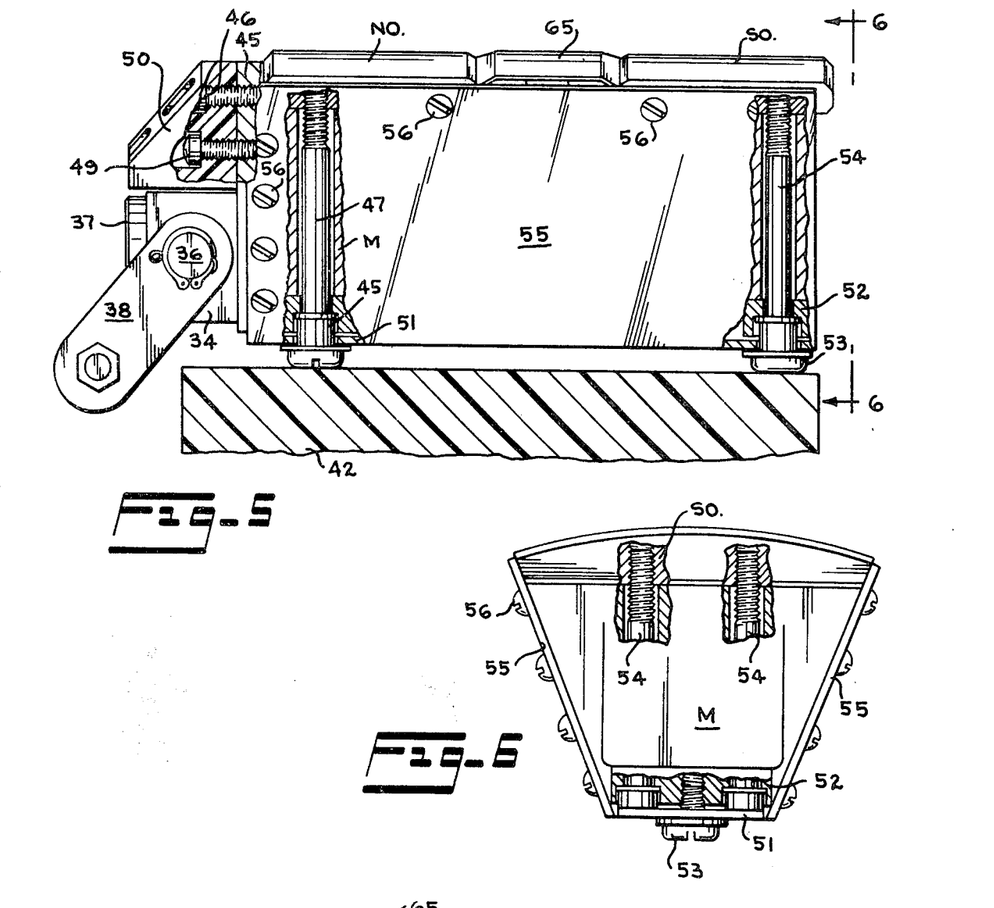
FIG. 5 is an enlarged view partly in elevation and partly in section showing one of the magnet assemblies and its mounting assembly.
FIG. 6 is a view in elevation taken along line 6—6 in FIG. 5.
Figure 7:
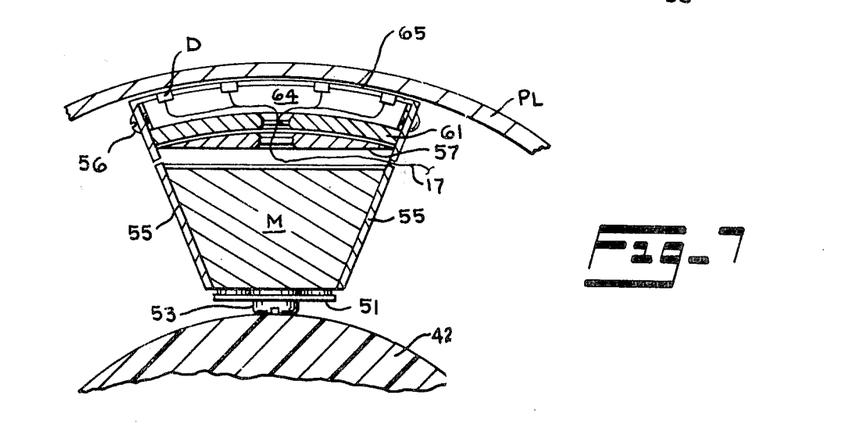
FIG. 7 is a cross-sectional view taken along line 7—7 in FIG. 3.

Each of the magnet assemblies 33 is pivotally mounted on the mandrel 28 by a mounting assembly which is adapted to pivot about three axes so that the magnet assembly can follow the interior wall of the pipeline. Each such mounting assembly includes a dual pivot block 34, shown in place in FIGS. 2, 3 and 5 and shown separately in perspective in FIG. 4. The pivot block 34 has a central bore 35 and has two coaxial pins 36 whose axes are substantially perpendicular to the axis of said bore 35. A threaded pivot pin 37 extends through bore 35 and not only secures the block 34 to the magnet assembly 33, but also enables the magnet assembly 33 to pivot about the longitudinal axis of the pin 37. The threads on pivot pin 37 may thus be said to be means for securing pivot block 34 to the magnet assembly 33. Each of a pair of spaced arms 38 has one of its ends pivotally connected to one of said pivot block pins 36 and the opposite end pivotally connected to one of the spaced lugs 39 by lug pin 40. The lugs 39 are secured to the plates 31 and 32 by suitable means such as nut and bolt assemblies 41 and thus the support 28 may be said to have lugs 39 thereon. Thus, each magnet assembly 33 can pivot about the three longitudinal axes of pins 36, 37 and 40.

Two annular resilient members 42 and 43, which are preferably made of open cell foam polyurethane, but may be made of foam rubber or similar elastomeric material, are mounted on the support or mandrel 28 between said mandrel 28 and each set of magnet assemblies 33. These polyurethane members 42 and 43 yieldingly urge the magnet assemblies 33 toward said pipeline PL and into contact with the interior wall of the pipeline PL, but permit the magnet assemblies to swing about pins 36, 37 and 40 and undergo radial movement inwardly and outwardly to accommodate variations in the internal diameter of the pipeline.

FIGS. 3, 5, 6 and 7 show the detailed structure of one of the magnet assemblies 33. Each assembly includes a junction plate 45 which is securely attached to magnetizing means such as U-shaped magnet M by bolts 46 and 47. Pivot pin 37 is threaded into a bore in the junction plate 45 and thus pivotally secures the pivot block 34 to the plate 45. For the purpose of locking the pivot pin 37 to the plate 45, set screw 48 impinges on the threads of the pivot pin 37. Bolts 46, together with bolts 49, also secure to the junction plate 45 a resilient bumper 50 which thus may be said to be secured to the downstream end of magnet assembly 33 and which protects the magnet assembly 33 against obstacles such as icicle welds projecting into the interior of the pipeline. A bottom plate 51 is secured to the junction plate 45 and to a spacer bar 52 by bolts 53. Bolts 54 attach the spacer bar 52 to the magnet M. A pair of side plates 55 are fastened to the magnet M by bolts 56. Thus, junction plate 45, bottom plate 51 and side plates 55 may be said to constitute a housing for magnet M. Applicants have discovered that in many circumstances it is appropriate to weld bottom plate 51 to junction plate 45, to spacer bar 52 and to an end plate (not shown) mounted across the upstream end of magnet M. This welding is preferable to the use of bolts 53, because vibrations may loosen bolts 53. For the same reason, it may be preferable to weld side plates 55 to bottom plate 51 and to said end plate (not shown).

The magnet M has a North pole NO and a South pole SO spaced apart from said pole NO. A base 57 is mounted below and between the poles NO and SO by bolts 58. The base 57 is provided with a pair of upward facing, spaced-apart recesses 59 for receiving resilient means such as springs 60. A detector holder 61, having a pair of downward facing, spaced-apart recesses 62 coaxial with recesses 59, is confined by poles NO and SO and is mounted for movement between the pipeline PL and base 57. The detector holder 61 engages springs 60 and is urged thereby toward pipeline PL. This detector holder 61 is formed with a third recess 63 which faces upwardly and within which the sensing means or magnetic flux detectors are disposed. In the preferred embodiment of the invention, the sensing means or flux detectors are twin magnetic diodes D and are mounted on the upper edge of a circuit board 64 which is connected to its associated electronic circuitry by conductor means 17. The circuit board 64 is retained in the recess 63 in desired orientation by a suitable dielectric potting compound, such as solid polyurethane, which fills the recess 63. A replaceable wear shim 65 is provided between detector holder 61 and pipeline PL to protect the holder and detectors from injurious contact with the interior wall of the pipeline. The shim 65 is removably fixed to the holder 61 by bolts 66. In the preferred embodiment, the twin magnetic diodes D are mounted to the recess 63 under the wear shim 65 and are spaced along a semi-circular path substantially perpendicular to the longitudinal axis of the pipeline, so that when the diodes are so mounted in each of the sixteen magnet assemblies 33, the entire wall of the pipeline will be inspected by the diodes. Applicants have discovered that in many circumstances it is preferable to insert a thin rubber strip, not shown in the drawings, between the shim 65 and the diodes D to protect the diodes from vibrations and other stresses which occur when the pig travels through the pipeline. The magnets M are preferably mounted uniformly in the magnet assemblies 33 so that their north poles NO are either all at the downstream end of the pig (as illustrated in the drawings) or all at the upstream end, so that they will magnetize the pipeline PL in a uniform direction. However, clearly there are many other possible configurations of the diodes and the magnets which do not depart from the spirit of the invention.

Thus, the polyurethane member 42 and the springs 60 yieldingly urge the diodes D toward the interior wall of the pipeline to increase their proximity to the flaws and to maintain them at a constant distance from the wall of the pipeline, thereby reducing variations in the signals caused merely by vibrations in the distance of the diodes from the wall of the pipeline, but at the same time accommodating any variations in the internal pipeline diameter. Applicants have found that in many circumstances it is appropriate to provide restraining means connecting the magnet assemblies 33 and the mandrel 28 in order to prevent the magnet assemblies 33 from pivoting outwardly into side openings, valves and other windings in the pipeline. In the preferred embodiment, these restraining means are straps connected to the upstream ends of the magnet assemblies and to the mandrel 28. These straps, which are not shown in the drawings, may be of leather or other suitable material. One strap is provided for each magnet assembly 33. For the purpose of facilitating the attachment of a strap to each magnet assembly 33, a pair of spaced-apart ears, not shown in the drawings, is welded to the upstream end of the inner surface of each bottom plate 51. To facilitate the attachment of the straps to the mandrel 28, a pair of spaced-apart ears, not shown in the drawings, is welded to the mandrel 28 near the upstream end of each magnet assembly 33. Each strap has two ends. One end is fastened by means of a pin extending through the end to the two ears on the magnet assembly 33; the other end is fastened by means of a pin extending through that end to the corresponding two ears on the mandrel 28. Each strap is of such a length as to permit the desired contact between its magnet assembly 33 and the wall of the pipeline P, but to prevent the entry of its magnet assembly into side openings and the like.

In the preferred embodiment of the invention, the diodes are oriented in a well-known manner so that they detect primarily only that component (the horizontal component) of the flux leakage which is substantially parallel to the longitudinal axis of the pipeline. Measuring primarily the horizontal component increases the longitudinal distance over which the measurement may be made, because a significant horizontal component parallels the longitudinal axis of the pipeline for a large distance inside the pipeline compared with the vertical component which is significant only relatively near the points of exit and entry from the pipeline. This measurement of the horizontal component is particularly useful in detecting those dangerous flaws with significant dimensions parallel to the longitudinal axis of the pipeline. In addition, measuring primarily the horizontal component makes the magnitude of the measurement independent of the angle that the flux leaves the pipeline, as opposed to the vertical component which is dependent on that angle. Further, this orientation simplifies the mechanics of mounting the diodes and enables the flux leakage to be measured at a relatively far distance from the interior surface of the pipeline wall, because the horizontal component is greatest at some distance inside the pipeline. In contrast, the vertical component extending perpendicular to the wall of the pipeline is maximum at the points of exit and entry from the pipeline. However, the magnetic diodes in any of the embodiments disclosed in this description may be oriented to detect primarily the horizontal component of the flux, primarily the vertical component, or any combination thereof.

FIG. 8 illustrates the well-known basic structure of a single magnetic diode. This single diode is a semiconductor device which changes its internal electrical resistance as a function of an external magnetic field. The diode comprises a germanium block with four zones: a P zone, an N zone, an intrinsic zone I and a recombination zone R. Negative charge lifetime is longer in zone I than in zone R so that, if negative charges are deflected into zone R by means of a magnetic field when current flows through the diode (in the direction indicated by the arrow), then the resistance of the diode increases. This resistance is also dependent on temperature and this temperature dependence may be substantially eliminated by the well-known technique of connecting a pair of single magnetic diodes electrically in series and arranging them in magnetic opposition to form a twin diode which may be said to be temperature independent. This technique is described in Telefunken's Semiconductor Application Report: Magnetic diodes AHY 10 and their application by H. Moser (Editor: AEG-Telefunken, Fachbereich, Halbleiter/Verbrieb D71 Heilbronn, Postfach 1042 W. Germany).

Figure 9:
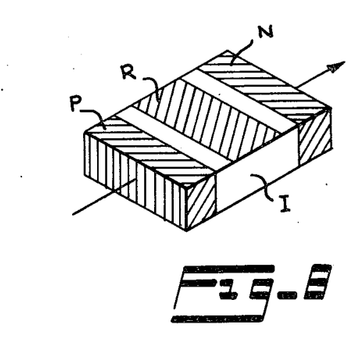
FIg. 9 is a schematic illustration of a configuration of the magnetic diodes and the electronic circuitry associated therewith, showing the diodes connected to the amplifiers according to the technique illustrated in FIG. 16.

FIG. 9 is a schematic illustration of a preferred arrangement of 16 twin magnetic diodes and the electronic circuitry associated with one of the 16 magnet assemblies 33. Thirty-two single magnetic diodes are disposed in pairs to form 16 twin diodes. As is shown most clearly in FIG. 16, the two single diodes of each twin diode are fixed in magnetic opposition in the sense that one single diode in each twin diode is of one magnetic orientation and the other single diode is of an opposite magnetic orientation. Further, the two single diodes of each twin diode are connected electrically in series so that the difference in the voltage drops across the two single diodes in each twin diode is substantially independent of temperature, as described above. This difference in voltage drops is a function of the magnetic flux impinging on the diodes and may be referred to as the output signal of the diodes. FIG. 9 shows four groups of twin diodes, the groups being indicated generally at 70, 80, 90 and 100, respectively and each group comprising four twin diodes, said twin diodes being represented by cross-hatched rectangles numbered 71–74, 81–84, 91–94 and 101–104, respectively. These twin diodes are arranged along a semi-circular path adjacent to the interior wall of a section of pipeline PL, said pipeline having two flaws designated 110 and 111 respectively.

Figure 16:
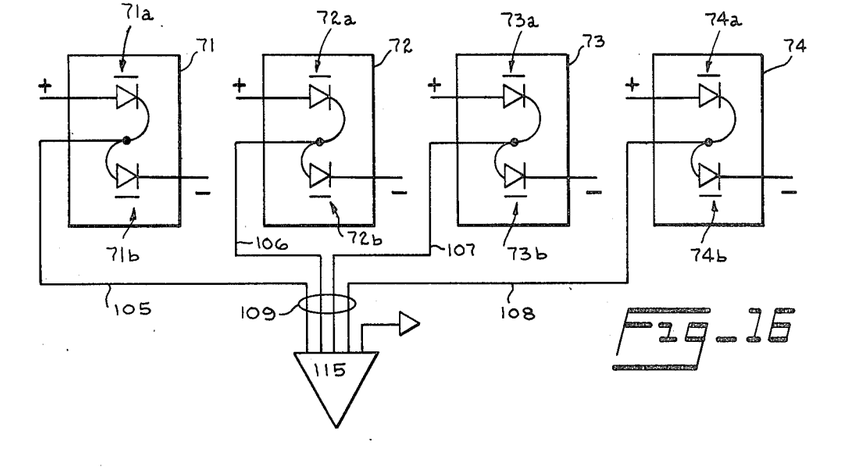
FIG. 16 is a schematic illustration showing the details of one technique for connecting the magnetic diodes to the amplifiers.

FIG. 16 shows the details of the electrical circuitry illustrated in FIG. 9 by showing in detail the wiring associated with each of the four twin diodes of group 70. In FIG. 16, the individual twin diodes 71–74 are shown to include pairs of single diodes identified respectively as 71a and 71b, 72a and 72b, 73a and 73b, and 74a and 74b. As discussed above, the two single diodes of each twin diode are arranged in magnetic opposition and are connected electrically in series, as taught in Telefunken's Semiconductor Application Report and as shown in FIG. 16. Lines 105, 106, 107 and 108 extend from twin diodes 71, 72, 73 and 74, respectively and, indicated collectively as 109 in FIGS. 9 and 16, connect twin diodes 71–74 with amplifier 115, as is discussed below. The other groups 80, 90 and 100 are wired in a similar manner.

Obviously, the four lines 105, 106, 107 and 108 in FIG. 16 could be connected to a common point so that the twin dides 71–74 are connected in parallel before their outputs are transmitted to amplifier 115. However, the embodiment shown in FIG. 16 is felt to be preferable and this parallel hookup will not be discussed in detail.

Figure 17:
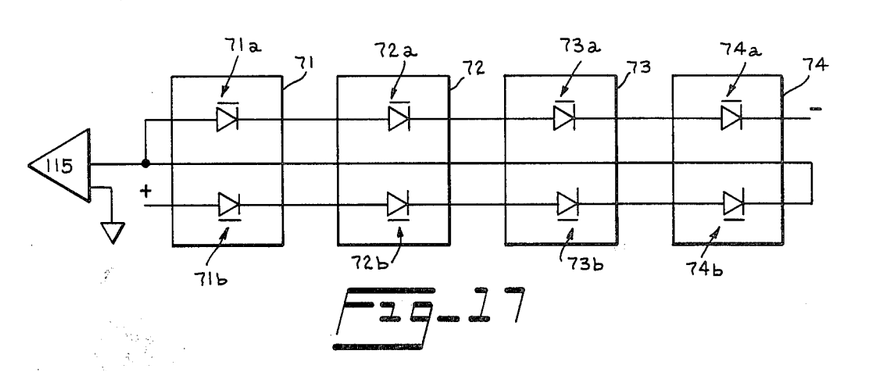
FIG. 17 is a schematic illustration showing the details of the preferred technique for connecting the magnetic diodes to the amplifiers.

FIG. 17 shows the preferred technique which applicants have discovered for connecting the magnetic diodes to the amplifiers. In FIG. 17, as in FIGS. 9 and 16, a plurality of single magnet diodes are disposed in pairs to form a plurality of twin diodes and are arranged in magnetic opposition in the sense that one single diode in each twin diode is of one magnetic orientation and the other single diode is of an opposite magnetic orientation. These twin magnetic diodes are spaced apart and have generally the same spatial orientation, so that the single diodes can be said to be two sets of single diodes with all of the single diodes in the first set being generally of one magnetic orientation and all of the single diodes of the second set being generally of an opposite magnetic orientation. For example, single diodes 71a, 72a, 73a and 74a in FIG. 17 can be said to comprise a first set of single diodes. Similarly, single diodes 71b, 72b, 73b and 74b can be said to comprise a second set of single diodes. The single diodes of the first set are connected in series. The single diodes of the second set are connected in series. These two sets are connected to each other in series and the connection between the two sets is connected to the amplifier 115.

As a result, the difference between the voltage drops across each set of diodes, which difference is the signal fed into the amplifier 115, is substantially independent of temperature, but is dependent on the magnetic flux impinging on the diodes and may be referred to as the output signal of the diodes.

The hookup illustrated in FIG. 17 is preferable to that illustrated in FIG. 16 because the FIG. 17 hookup requires less power and a less sophisticated amplifier than that shown in FIG. 16. However, either hookup may be used within the scope of this invention. Thus, the electrical connections illustrated in and discussed in connection with FIGS. 16 and 17 may be referred to as electrical connections which are such that the output signals of the diodes are substantially independent of temperature.

Figure 18:
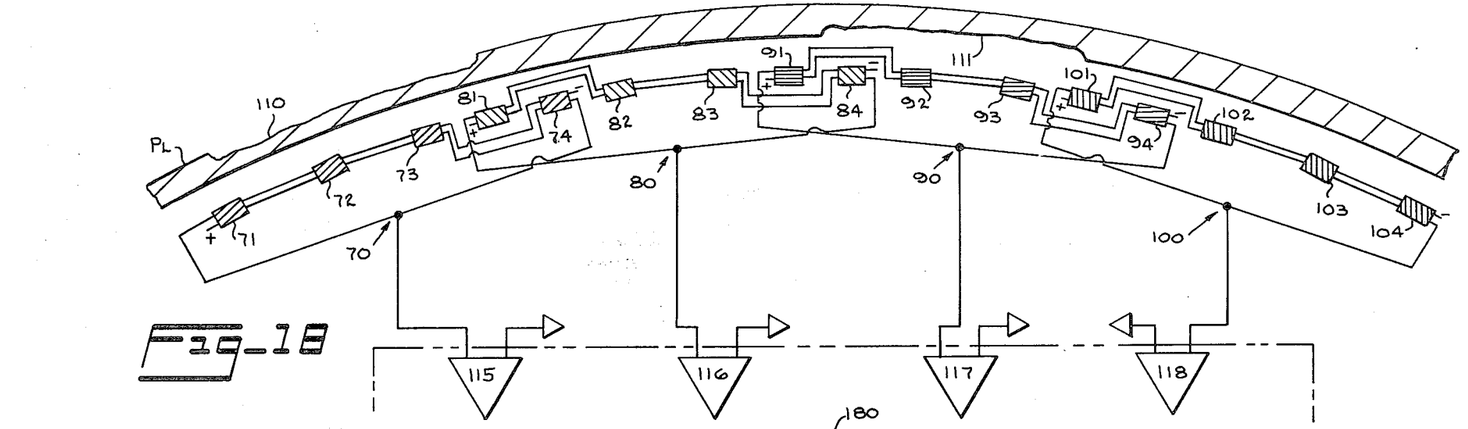
FIG. 18 is a schematic illustration of the preferred configuration and connection of the magnetic diodes to the amplifiers.

FIG. 18 shows twin diodes 71–74, 81–84, 91–94 and 101–104 spaced apart as shown in FIG. 9, but wired according to the technique of FIG. 17. It will be understood that amplifiers 115–118 in FIG. 18 are also shown as amplifiers 115–118 in FIG. 9 and are connected to filter 120 and the other components illustrated in FIG. 9.

In FIGS. 9 and 18, flaw 111 is of the minimum size sought to be detected. Because flaws below a minimum size do not pose a significant threat to the pipeline and are not required by the United States Department of Transportation to be corrected, one may detect only those flaws equal to or above that minimum size. The present device contemplates detecting primarily transverse oriented internal and external flaws such as seams, cracks, pits, hard spots and mechanical damage, although clearly the invention may be used to detect flaws of any orientation. The apparatus is designed primarily to detect each flaw whose transverse dimension is greater than three-eighths of one inch.

The twin diodes in each group are spaced along the semi-circular path adjacent the pipeline wall and adjacent each other so that the distance between the centers of any two adjacent twin diodes in each group is no more than approximately one-half the longest linear dimension along said path of flaw 111. As illustrated in FIGS. 9 and 18, this linear dimension is transverse to the longitudinal axis of the pipeline. For most pipelines in use today, detecting flaws of the size described above will involve spacing the twin diodes approximately ¼ inch to ⅜ inches apart, but obviously this spacing and the size and character of the flaws sought to be detected can be changed without departing from the scope of the invention. Further, as illustrated in FIGS. 9 and 18, the four groups, 70, 80, 90 and 100 of the twin diodes are spaced along the path in overlapping relationship so that at least one of the twin diodes in each group is between at least two twin diodes of each adjacent group. For example, the group 70 is adjacent only to the group 80 and twin diode 74 is spaced between twin diodes 81 and 82. The group 80 is adjacent groups 70 and 90; twin diode 81 is between twin diodes 73 and 74 and twin diode 84 is between twin diodes 91 and 92. This spatial relationship is such that as the four groups are moved along the pipeline, the magnetic flux from each flaw of a size sought to be detected and passed over by the magnet assembly illustrated in FIGS. 9 and 18 will be detected by at least two twin diodes in one of the four groups, thus producing a strong signal for recordation and interpretation. As indicated above, in the preferred embodiment of the invention, the diodes are placed in each magnet assembly 33 so that the entire circumference of the pipeline will be inspected.

Even in the absence of flaws or external sources of magnetic flux, typically some flux will flow through the diodes and between the poles NO and SO. By definition, zero flux level is that level of magnetic flux measured by the diodes when the pig is in a flawless section of pipeline remote from sources of flux external to the pig. Also by definition, diode signals corresponding to measured flux above zero level are positive and diode signals corresponding to measured flux below zero level are negative. Thus, flaws will cause flux to leak out of the pipeline PL into the region between poles NO and SO and will give rise to positive diode signals.

FIG. 9 also shows in schematic the electronic circuitry associated with each group of twin diodes. Standard amplifiers 115, 116, 117 and 118 are associated with the groups 70, 80, 90 and 100 respectively so that the positive and negative signals from each group are transmitted to one of these amplifiers. The positive and negative signals from the four amplifiers 115–118 are then transmitted to a first filter means such as a standard filter 120 which passes to the next stage at any given time only a selected number, such as one or two or three, of the larger of the positive signals from the amplifiers. In the preferred embodiment, filter 120 passes only the largest of these positive signals from the amplifiers. Such filters are well-known in the art, are sometimes referred to as amplitude selective gates and may be purchased from many sources. For example, a filter of the character of Fairchild Semiconductor FSA 1411M monolithic diode array, made by Fairchild Camera and Instrument Corporation of Mountain View, Calif., may be used. Thus, after the filter 120, there is only one flaw signal channel for each magnet assembly 33. This filtering out of the smaller signals greatly simplifies the task of processing, recording and interpreting the signals from the magnetic diodes, with attendant reduction in the amount, cost and weight of equipment required. Recording only the largest signal at any one time from the four groups of twin diodes in each magnetic assembly does not materially affect the usefulness of the information gathered by the inspection apparatus, because the condition of the pipeline at a given point therealong can be evaluated accurately without knowledge of the presence or absence of adjacent but lesser flaws.

The signal from the filter 120 is transmitted to a standard voltage controlled oscillator 121 for the purpose of converting amplitude variations in the signal to frequency variations and thereby reducing the noise introduced by the recording and playback operation, which operation will be explained below. This noise constitutes random components of the signal not associated with flaws. The signal is then transmitted from the voltage controlled oscillator 121 to a recording means or recorder 122 such as a standard magnetic tape deck. Recorder 122 has a plurality of channels and permanently records and stores within the inspection apparatus on 16 separate channels the sixteen separate flaw signals from the 16 voltage controlled oscillators associated with the 16 magnet assemblies.

Figure 13:
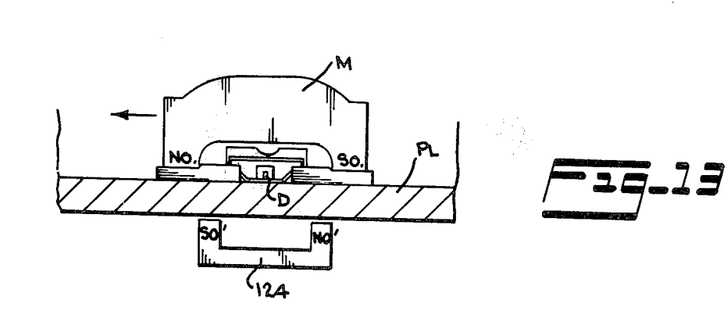
FIG. 13 is a view partly in elevation and partly in section of the placement of a magnetic marker with respect to the pipeline and with respect to the inspection apparatus for locating flaws detected by the apparatus.

As an aid in determining the location of detected flaws, magnetic markers are placed at selected locations along and exterior to the pipeline PL. These markers are preferably magnets, but may be of any material, such as permeable iron, which will influence the flow of magnetic flux in the interior of the pipeline when the pig magnets M pass by the markers. For example, in FIG. 13, marker 124 is a permanent magnet and is oriented with respect to the pig magnet M to reduce the magnetic flux flow which is induced through the interior of the pipeline PL by the pig magnet M. In FIG. 13, pig magnet M and market 124 are oriented in opposed relationship in the sense that the pole NO' of marker 124 is disposed upstream of pole SO', whereas pig pole NO is disposed downstream of pole SO. Thus, as the pig magnet M passes by marker 124, the induced flux measured by the diodes D in the interior of the pipeline first increases, then decreases, then increases again, as marker 124 alters the flux flow between poles NO and SO. As stated above, zero flux level is defined as that level of magnetic flux measured by the diodes when the pig is in a flawless section of the pipeline remote from external sources of flux (such as magnetic markers). Also by definition above, diode signals corresponding to flux above zero flux level are positive and those corresponding to flux below zero flux level are negative. As magnet M approaches marker 124, the interaction between poles NO and NO' will cause the flux measured by the diodes to increase above zero flux level because it will cause more flux to flow in the region of the diodes between poles NO and SO. When the magnet M passes over marker 124, the magnetic flux flowing between poles NO and SO will tend to be shunted through the marker, thus reducing below zero level the flux measured by the diodes D. As pole SO passes over SO', the interaction between poles SO and SO' will cause another increase above zero flux level in the flux measured by the diodes D. Thus, the magnetic markers will give rise to predominantly negative signals from the diodes, whereas the flaws will give rise to predominantly positive signals.

As explained above, the positive and negative signals from the diodes will be transmitted through filter 120 which passes only the largest positive signals from the four amplifiers. However, the signals from one of the amplifiers in each magnet assembly 33, for example amplifier 117 in FIGS. 9 and 18, are tapped before they get to filter 120 and are passed through a second filter means such as electric diode 123 which passes only the negative signals to a third filter means 125. As is illustrated diagrammatically in FIG. 9, this third filter 125 also receives seven other negative marker signals which have been tapped from the seven other amplifiers 117 in each of the seven other magnet assemblies 33 in this magnet ring. The filter 125 passes to the next stage at any given time only a selected number, such as one or two or three, of the more negative of these marker signals. In the preferred embodiment, filter 125 is of the character of Fairchild Semiconductor FSA 1410M monolithic diode array and passes only the most negative of these marker signals to a standard inverter amplifier 126 which further amplifies them and inverts them so that they will be recorded and visually presented as positive signals. As explained above, the flaw signals will be recorded and visually presented as positive signals; this inversion of the marker signals will thus cause all signals to be recorded and visually presented as positive signals, thus simplifying their processing and interpretation. The inverted marker signals are then passed to a second standard voltage controlled oscillator 127 and from there to the recorder 122 for recordation on a channel next to the channels the flaw signals. Thus, in the entire inspection apparatus, there are sixteen channels for flaw signals with one filter and one voltage controlled oscillator for each channel, two channels for marker signals with one filter and voltage controlled oscillator for each channel, and one recorder for all eighteen channels. However, obviously the number of magnet assemblies, channels, recorders and other components may be changed without departing from the spirit of the invention.

In the preferred embodiment, the location of flaws is determined by placing the magnetic marker 124 in opposed relationship to pig magnet M to first increase, then decrease, then increase again the flux measured by diodes D. However, clearly the magnetic markers may be placed along the pipeline with any substantially uniform orientations with respect to the pipeline (and thus with respect to the pig magnets) to cause substantially uniform influences on the flux detected by the diodes D in the interior of the pipeline. For example, marker 124 could be oriented so that pole NO' is disposed downstream of pole SO' so that, as magnet M passes by marker 124, the flux measured by the diodes first decreases, then increases, then decreases.

Figure 12:
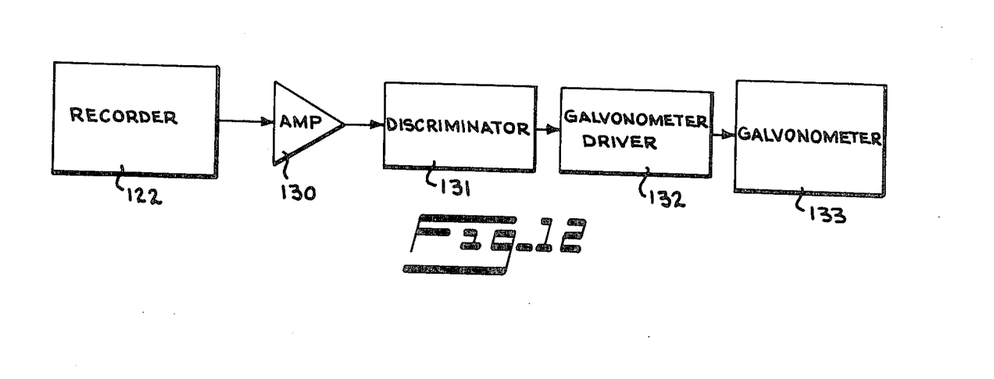
FIG. 12 is a schematic illustration of the electronic playback circuitry for visually presenting the signals from the magnetic diodes.

FIG. 12 illustrates diagrammatically the playback processing of the signals after the run of the inspection apparatus or pig is completed. The signals are transmitted from recorder 122 to a standard amplifier 130 to a standard discriminator 131 to a standard galvonometer driver 132 to a standard galvonometer 133. The discriminator 131 converts frequency variations of the signals to amplitude variations for ease of visual interpretation. The galvonometer converts the electrical signals into visual form as shown in the strip chart 134 illustrated in FIG. 14. Preferably the galvonometer includes a light beam impinging on a light-sensitive chart, but the galvonometer may include a mechanical stylus or any other device for marking the strip chart.

Figure 14:
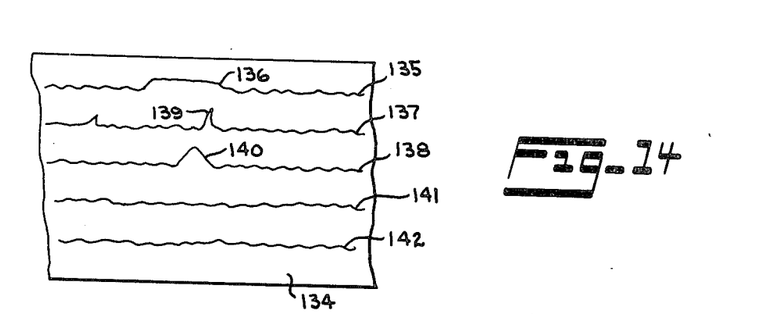
FIG. 14 is a view in elevation of a strip chart recording of signals from the diodes.

Thus, in the preferred embodiment of the invention there will be nineteen traces on strip chart 134: one for the flaw signals from each magnet assembly, one for the marker signals from each ring and one for the signals from the odometer. FIG. 14 illustrates only five of these traces. Trace 135 shows a typical negative marker signal 136 which, as explained above, has been inverted by inverter amplifier 126 to appear as a positive signal for ease of processing and interpretation. Traces 137 and 138 show typical flaw indications 139 and 140; traces 141 and 142 show typical background noise signals.

In operation, the magnetic markers are placed at selected locations along the pipeline and the inspection apparatus is placed in the pipeline. As explained, the magnetic markers are oriented along the pipeline in opposed relationship to the magnets in the inspection apparatus. Fluid pressure in the pipeline propels the inspection apparatus therethrough and the magnets and magnetic diodes of the inspection apparatus, yieldingly urged outwardly by the polyurethane members, traverse the interior wall or surface of the pipeline in sufficient proximity to magnetize successive sections of the pipeline and detect flux leakage caused by flaws in the pipeline. The signals from the magnetic diodes are processed and recorded on magnetic tape within the inspection apparatus; positive signals indicating flaws are recorded on sixteen channels; negative signals from the magnetic markers are inverted and recorded on two additional channels; signals from the odometer are recorded on a nineteenth channel. At the end of the run, the magnetic tape is played back, the signals are converted from frequency variations to amplitude variations and are recorded in visual form on a strip chart by a light beam galvonometer. The strip chart may then be interpreted to analyze the condition of the pipeline and the location of the detected flaws.

Thus, it can be seen from the foregoing that an invention has been provided which inspects immovable test objects by magnetic diode sensing means. These magnetic diodes are sensitive, simple, inexpensive, have low power requirements and can measure flux leakage independently of the speed of the diodes with respect to the flux leakage. Further, the diodes and magnets constantly are kept in sufficiently close proximity to the wall of the pipeline to magnetize and test the pipeline by the mounting assemblies which pivot about three axes and by the light, compact, easy-to-maintain and inexpensive polyurethane members. In addition, the magnetic markers are detected by the same diodes which detect the flux leakage caused by flaws without the necessity of providing additional sensing means to detect the markers.

ALTERNATIVE EMBODIMENTS

Figure 10:
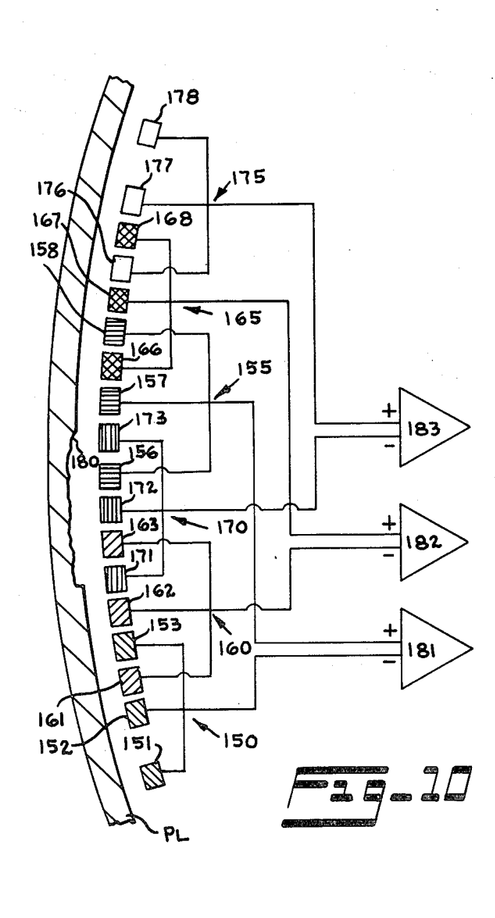
FIG. 10 is a schematic illustration of another embodiment of the invention showing the position of the magnetic diodes with respect to the interior wall of the pipeline and the associated electronic circuitry which functions to eliminate the effects of unwanted magnetic flux background and which connects the diodes to the amplifiers according to the technique illustrated in FIG. 16.
Figure 19:
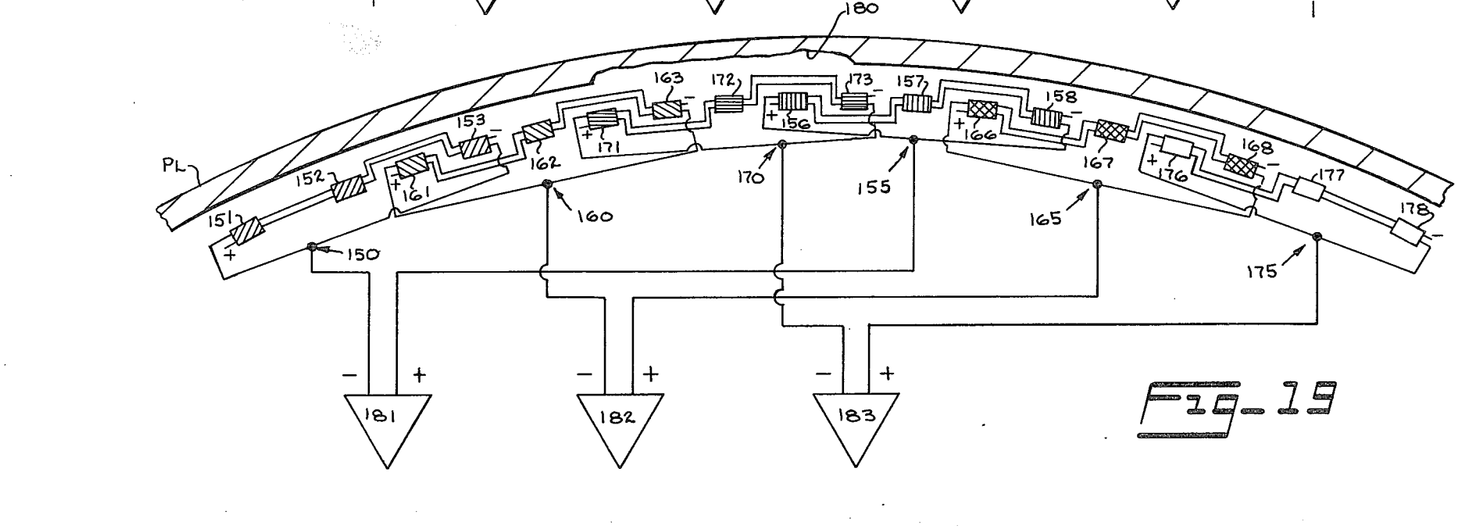
FIG. 19 is a schematic illustration of another embodiment of the invention showing the position of the magnetic diodes with respect to the interior wall of the pipeline and the associated electronic circuitry which functions to eliminate the effects of unwanted magnetic flux background and which connects the diodes to the amplifiers according to the technique illustrated in FIG. 17.

FIGS. 10 and 19 disclose alternative embodiments of the invention where six groups of three twin diodes each are spaced in overlapping relationship similar to that of FIGS. 9 and 18, but nonadjacent groups are connected in pairs to determine and record the difference between the magnetic fluxes detected by said pairs. This result is accomplished by transmitting the signals from said nonadjacent groups to differential means such as a differential amplifier which will compare the two signals and transmit only the difference between the two signals for recordation and interpretation. This technique is useful for filtering out the effects both of background magnetic flux not related to the flaws and of changes in the diode signals caused by changes in the distance between the diodes and the pipeline wall.

FIG. 10 illustrates the diodes connected according to the technique of FIG. 16. FIG. 19 illustrates the diodes connected according to the technique of FIG. 17.

In the examples in FIGS. 10 and 19, there are six groups of three twin diodes each, indicated generally at 150, 155, 160, 165, 170 and 175. These groups each include twin diodes numbered 151–3, 156–8, 161–3, 166–8, 171–3 and 176–8 respectively. As shown, the twin diodes in each group are spaced along a path adjacent pipeline PL with flaw 180, the smallest flaw sought to be detected, so that the distance between the centers of any two adjacent twin diodes in that group is no more than approximately one-half the length of flaw 180. Further, as in the embodiments of FIGS. 9 and 18, at least one of the twin diodes in each group is between at least two of the twin diodes of each adjacent group. The signals from groups 150 and 155 are transmitted to differential means such as a standard differential amplifier 181; the signals from groups 160 and 165 are transmitted to a standard differential amplifier 182; the signals from groups 170 and 175 are transmitted to a standard differential amplifier 183. At any point in time, these differential amplifiers transmit for further processing, recordation and interpretation (as shown in FIG. 9) only the difference between the signals which they receive from their respective pairs of groups. As in FIG. 9, a first filter means passes only a selected number, such as one or two, of the larger of the positive signals from the amplifiers 181, 182 and 183. In the preferred embodiment, such filter means passes only the largest of these positive signals from the amplifiers. Thus, a differential means is connected to at least two groups of twin diodes, constituting a plurality of twin diodes, and to a recording means for determining and recording the difference between signals from said two groups, whereby the difference between the magnetic flux detected by said groups may be determined and reecorded.

Figure 11:
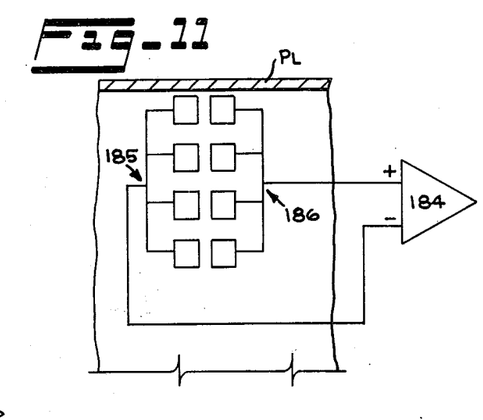
FIG. 11 is a schematic illustration of another embodiment of the invention comprising a configuration of the magnetic diodes whereby the magnetic fluxes at two longitudinally spaced-apart points along the interior wall of the pipeline may be measured and compared and whereby the diodes are cconnected to the amplifiers according to the technique illustrated in FIG. 16.
Figure 20:
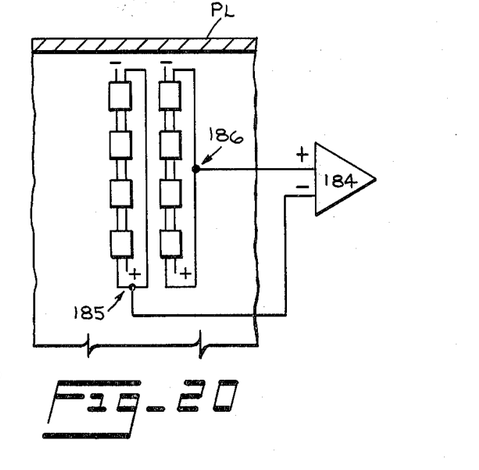
FIG. 20 is a schematic illustration of another embodiment of the invention comprising a configuration of the magnetic diodes whereby the magnetic fluxes at two longitudinally spaced-apart points along the interior wall of the pipeline may be measured and compared and whereby the diodes are connected to the amplifiers according to the technique illustrated in FIG. 17.

FIGS. 11 and 20 illustrate yet another embodiment of the invention to eliminate the effects of background flux and changes in the distance between the magnetic diodes and pipeline wall. In FIGS. 11 and 20, differential means such as standard differential amplifier 184 is connected to groups 185 and 186, each group comprising four twin diodes. FIG. 11 illustrates the twin diodes connected according to the technique of FIG. 16. FIG. 20 illustrates the diodes connected according to the technique of FIG. 17. Instead of lying along a continuous curved path, groups 185 and 186 are spaced along substantially parallel, spaced-apart curved paths and measure the flux at points spaced along the longitudinal axis of the pipeline PL. Obviously more than one group could be spaced along either of the paths. Of course, the signals are transmitted from amplifier 184 for further processing, recordation and interpretation as shown in FIG. 9. As in FIG. 9, a first filter means passes only a selected number of the larger of the positive signals from the amplifiers. Thus, at least two of the groups along the paths are connected to said differential means, one of said groups being from one of said paths and the other of said groups being from the other of said paths and said differential means is connected to the recording means, whereby the differences between the magnetic flux along the two paths may be determined and recorded.

Figure 15:
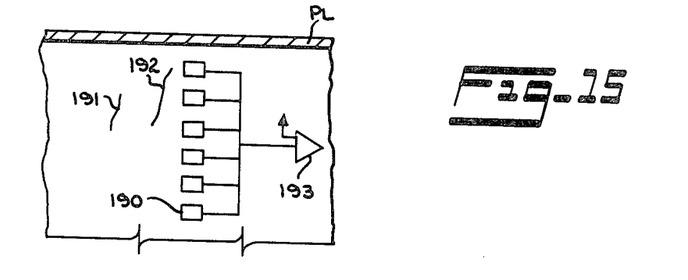
FIG. 15 is a schematic illustration showing a relatively simple arrangement of the magnetic diodes connected to the amplifiers according to the technique illustrated in FIG. 16.
Figure 21:
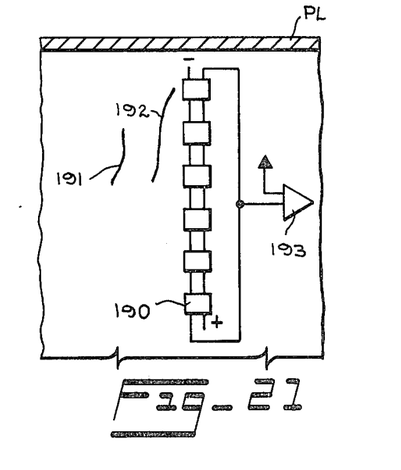
FIG. 21 is a schematic illustration showing a relatively simple arrangement of the magnetic diodes connected according to the technique illustrated in FIG. 17.

FIGS. 15 and 21 illustrate a relatively simple embodiment of the invention comprising a plurality of twin magnetic diodes 190 spaced along a curved path substantially perpendicular to the longitudinal axis of the pipe to detect flaws such as cracks 191 and 192. In FIG. 15, the twin diodes are connected as in FIG. 16. In FIG. 21, the diodes are connected according to the teaching of FIG. 17. The signals from twin diodes 190 are transmitted to a standard amplifier 193 and to other electric components as illustrated in FIG. 9 and discussed in connection therewith. As in FIG. 9, a first filter means passes only a selected number of the larger of the positive signals from the amplifiers. The twin diodes preferably are spaced apart so that the centers of adjacent twin diodes are no farther apart than approximately the longest linear dimension along said path of the smallest flaw sought to be detected, illustrated as crack 191 in FIGS. 15 and 21, so that the flaw will not pass between said twin diodes and go undetected, but will be detected by at least one twin diode when said twin diodes move over said flaw. The twin diodes may, of course, be spaced closer together to increase the chance of the flaw's being detected by two or more twin diodes and thus generating a stronger flaw signal. For example, in FIGS. 15 and 21, if crack 192 is considered to be the smallest flaw sought to be detected, then the twin diodes 190 are spaced along a path so that the centers of adjacent twin diodes are no farther apart than approximately one-half the longest linear dimension along said path of the smallest flaw sought to be detected, whereby said smallest flaw will be detected by at least two twin diodes when said diodes move over said flaw.

The foregoing disclosure and description of the invention are illustrative and explanatory thereof, and various changes in the size, shape and materials, as well as in the details of the illustrated construction may be made within the scope of the appended claims without departing from the spirit of the invention.

What is claimed is:

1. A method of determining the location of flaws in a magnetizable pipeline, said method including the steps of:

causing a magnetizing means to traverse the interior of the pipeline in sufficiently close proximity to the pipeline to induce magnetic flux flow in the pipeline and in the interior of the pipeline;

placing a magnetic marker at a selected location along the pipeline and exterior to the pipeline and oriented in opposed relationship with respect to said magnetizing means, so that said marker causes first an increase, then a decrease, then an increase in said flux flow in the interior of the pipeline as said magnetizing means passes by said marker;

detecting said decrease;

recording said decrease;

detecting variations in said magnetic flux flow in the interior of the pipeline, which variations are caused by flux leakage resulting from flaws in the pipeline;

recording said variations; and correlating said decrease with said variations to determine the positions of detected flaws with respect to said selected location.

2. A method of determining the location of flaws in a magnetizable pipeline, said method including the steps of:

causing a magnetizing means to traverse the interior of the pipeline in sufficiently close proximity to the pipeline to induce magnetic flux flow in the pipeline and in the interior of the pipeline adjacent said magnetizing means;

placing a plurality of magnetic markers at selected locations along the pipeline and exterior to the pipeline, which markers cause variations of said flux flow in the interior of the pipeline adjacent said magnetizing means, said markers oriented in an opposed magnetic relationship to said magnetizing means;

detecting variations of said flux flow in the interior of the pipeline adjacent said magnetizing means, which variations are caused by flux leakage resulting from flaws in the pipeline or from said magnetic markers;

correlating said variations caused by said flaws with said variations caused by said markers to determine the positions of detected flaws with respect to said selected locations.

3. The method of claim 2 including the steps of recording said variations.

4. The method of claim 3 including the steps of generating signals caused by said variations; separating the signals caused by variations associateed with said flaws from the signals caused by variations associated with said markers.

5. A method of determining the location of flaws in a magnetizable pipeline, said method including the steps of:

causing a magnetizing means to traverse the interior of the pipeline in sufficiently close proximity to the pipeline to induce magnetic flux flow in the pipeline and in the interior of the pipeline adjacent said magnetizing means;

placing a plurality of magnetic markers at selected locations along the pipeline and exterior to the pipeline, which markers cause influences on said flux flow in the interior of the pipeline adjacent said magnetizing means, said markers oriented in an opposed magnetic relationship to said magnetizing means;

detecting said influences;

detecting variations in said flux flow in the interior of the pipeline adjacent said magnetizing means, which variations are caused by flux leakage resulting from flaws in the pipeline;

correlating said influences with said variations to determine the positions of detected flaws with respect to said selected locations.

6. The method of claim 5 including the steps of recording said influences and said variations.

7. A method of determining the location of flaws in a magnetizable pipeline, said method including the steps of:

causing a magnetizing means having north and south poles to traverse the interior of the pipeline in sufficiently close proximity to the pipeline to induce magnetic flux flow in the pipeline and in the interior of the pipeline adjacent said magnetizing means;

placing a plurality of magnetic markers having north and south poles at selected locations along the pipeline and exterior to the pipeline, which markers cause influences on said flux flow in the interior of the pipeline adjacent said magnetizing means, said markers oriented in an opposed magnetic relationship to said magnetizing means so that like poles of said magnetizing means and of said magnetic markers will simultaneously be in close proximity to each other;

detecting said influences;

detecting variations in said flux flow in the interior of the pipeline adjacent said magnetizing means, which variations are caused by flux leakage resulting from flaws in the pipeline, said variations being of opposite polarity from said influences because of the opposed magnetic orientation of said markers to said magnetizing means;

correlating said influences with said variations to determine the positions of detected flaws with respect to said selected locations.

8. The method of claim 7 including the steps of recording said influences and said variations.

* * * * *